United States Patent
Ikeda et al.

(10) Patent No.: US 6,177,541 B1
(45) Date of Patent: Jan. 23, 2001

(54) PROCESS FOR PRODUCING AN ISOCYANURATE DERIVATIVE

(75) Inventors: Hisao Ikeda; Toshinari Koda; Yasuhiro Gunji, all of Funabashi (JP)

(73) Assignee: Nissan Chemical Industries, Ltd., Tokyo (JP)

( * ) Notice: Under 35 U.S.C. 154(b), the term of this patent shall be extended for 0 days.

(21) Appl. No.: 09/362,910

(22) Filed: Jul. 29, 1999

(30) Foreign Application Priority Data

Aug. 20, 1998 (JP) .................................................. 10-234423

(51) Int. Cl.[7] .............................. C08F 6/06; C08G 18/82
(52) U.S. Cl. ..................... 528/487; 528/503; 528/422; 528/423; 528/72; 528/80; 528/287
(58) Field of Search ..................... 528/422, 423, 528/487, 503, 72, 80, 287

(56) References Cited

U.S. PATENT DOCUMENTS

| | | |
|---|---|---|
| 4,988,395 | 1/1991 | Taguchi et al. . |
| 5,116,945 | 5/1992 | Osawa et al. . |
| 5,892,065 | 4/1999 | Tsukamoto et al. . |

*Primary Examiner*—Duc Truong
(74) *Attorney, Agent, or Firm*—Oblon, Spivak, McClelland, Maier & Neustadt, P.C.

(57) ABSTRACT

A process for producing an isocyanurate derivative of the formula (1):

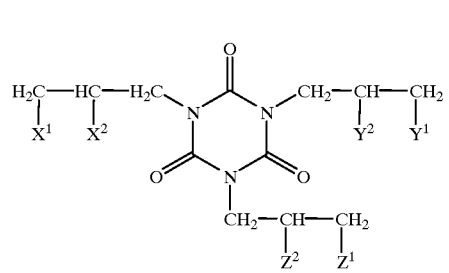

wherein one each of $X^1$, $X^2$, of $Y^1$, $Y^2$ and of $Z^1$, $Z^2$, a R COO group and the other is a OH group and each R is a $C_{1-7}$ organic group, having an ionic chlorine atom content of from 0.1 to 5 ppm, which comprises reacting (A) tris-(2,3-epoxypropyl) isocyanurate containing from 10 to 3,000 ppm of hydrolyzable chlorine and (B) a carboxyl group-containing compound, in the presence of (C) an arylphosphine and/or a phosphonium salt comprising a non-halogen anion, until the concentration of the epoxy group in the reaction solution decreases to a 0.3 to 0.6 eq/kg, and then maintaining the reaction solution at 80 to 130° C. for H hours, where $0.2 \times 2.5^n \leq H \leq 2 \times 2.5^n$, where $n=0.1(110-T)$, where T is the temperature (° C.), to bring the epoxy group concentration in the reaction solution to a level of less than 0.1 eq/kg.

7 Claims, No Drawings

PROCESS FOR PRODUCING AN ISOCYANURATE DERIVATIVE

BACKGROUND OF THE INVENTION

1. Field of the Invention

The present invention relates to an isocyanurate derivative obtainable by a reaction of tris-(2,3-epoxypropyl) isocyanurate with a carboxyl group-containing compound, which is excellent in heat resistance. This isocyanurate derivative is a highly viscous liquid which has heat resistance attributable to a triazine ring and water-solubility attributable to hydroxyl groups and which contains little ionic chlorine, and it is useful as e.g. a thickening agent in an electric or electrical field for e.g. a flux composition.

2. Discussion of Background

As a catalyst for a reaction of an epoxy compound such as tris-(2,3-epoxypropyl) isocyanurate, with a carboxyl group-containing compound, a tertiary amine or a quaternary ammonium salt is commonly used, but such a catalyst is likely to often bring about a ring-opening polymerization reaction of epoxy groups as a side reaction to form an insoluble substance. JP-A-2-275867 discloses a reaction product of tris-(2,3-epoxypropyl) isocyanurate with a carboxyl group-containing compound, and a process for its production. However, if a quaternary ammonium salt is used as the catalyst disclosed in the Examples, or if the reaction is carried out at a high temperature in the absence of a catalyst, a part of tris-(2,3-epoxypropyl) isocyanurate undergoes ring-opening polymerization to form an insoluble substance as a by-product. Since the product is highly viscous liquid, there has been a problem that it has to be diluted with a solvent or heated to a high temperature to reduce the viscosity and remove the insoluble substance by filtration while it is still hot. Further, if a quaternary ammonium chloride is used, and if it remains in the product, it may adversely affect the electrical properties, since it is a substance having ionic chlorine.

Further, epichlorohydrin is used as a starting material in the process for producing tris-(2,3-epoxypropyl) isocyanurate, and if an ethylene chlorohydrin moiety as an epoxy precursor is present, such a moiety will remain in the molecule as hydrolyzable chlorine. This hydrolyzable chlorine does not usually change to ionic chlorine hazardous to the field of electronic and electric materials, even when treated at a high temperature for a long time. This may be explained in such a way that even if dehydrochlorination takes place to form ionic chlorine, such ionic chlorine will immediately undergo an addition reaction with an epoxy group present in the vicinity to again become to be an ethylene chlorohydrin moiety. Accordingly, usual tris-(2,3-epoxypropyl) isocyanurate contains no ionic chlorine.

However, when a reaction product of tris-(2,3-epoxypropyl) isocyanurate with a carboxyl group-containing compound is produced, formation of ionic chlorine has been observed surprisingly.

Namely, it has been difficult to obtain a reaction product of tris-(2,3-epoxypropyl) isocyanurate with a carboxyl group-containing compound, which contains little ionic chlorine and is free from an insoluble substance, by the conventional technology.

SUMMARY OF THE INVENTION

It is an object of the present invention to provide a novel process for producing an isocyanurate derivative which is free from an insoluble substance and transparent and which has very little ionic chlorine content, for the production of an isocyanurate derivative as an addition reaction product with a carboxyl group-containing compound, by using, as a starting material, tris-(2,3-epoxypropyl) isocyanurate containing hydrolyzable chlorine.

In the first aspect, the present invention provides a process for producing an isocyanurate derivative of the formula (1):

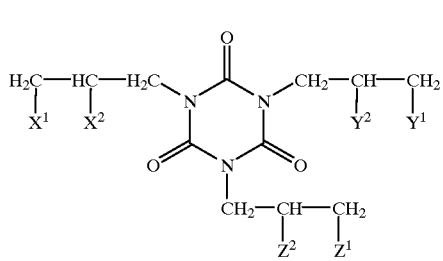

(1)

wherein either one of $X^1$ and $X^2$ is a $R^1COO$ group and the other is a OH group, either one of $Y^1$ and $Y^2$ is a $R^2COO$ group and the other is a OH group, either one of $Z^1$ and $Z^2$ is a $R^3COO$ group and the other is a OH group, and each of $R^1$, $R^2$ and $R^3$ is a $C_{1-7}$ organic group, having an ionic chlorine atom content of from 0.1 to 5 ppm, which comprises a first step of forming a reaction solution containing (A) tris-(2,3-epoxypropyl) isocyanurate containing from 10 to 3,000 ppm of hydrolyzable chlorine and (B) a carboxyl group-containing compound in the presence of (C) an arylphosphine and/or a phosphonium salt comprising a non-halogen anion, in such a ratio that the carboxyl group in component (B) is from 1.02 to 1.50 mols per mol of the epoxy group in component (A), and then carrying out a reaction until the concentration of the epoxy group in the reaction solution decreases to a level of from 0.3 to 0.6 eq/kg, and a second step of maintaining the reaction solution at a temperature within a range of from 80 to 130° C. for H hours, provided $0.2 \times 2.5^n \leq H \leq 2 \times 2.5^n$, where n=0.1(110−T) where T is the temperature (° C.), to bring the concentration of the epoxy group in the reaction solution to a level of less than 0.1 eq/kg.

In the second aspect, the present invention provides the process for producing an isocyanurate derivative according to the first aspect, wherein the carboxyl group-containing compound of component (B) is at least one member selected from the group consisting of a $C_{2-4}$ monocarboxylic acid, a $C_{2-8}$ polycarboxylic acid and a $C_{2-8}$ hydroxycarboxylic acid.

In the third aspect, the present invention provides the process for producing an isocyanurate derivative according to the first aspect, wherein the carboxyl group-containing compound of component (B) is acetic acid, hydroxyacetic acid, lactic acid, or a mixture thereof.

In the fourth aspect, the present invention provides the process for producing an isocyanurate derivative according to any one of the first to third aspects, wherein in the first step, the reaction is carried out in such a manner that component (B) having component (C) dissolved therein, is added to component A).

In the fifth aspect, the present invention provides the process for producing an isocyanurate derivative according to any one of the first to third aspects, wherein in the first step, the reaction is carried out in such a manner that component (C) dissolved in an aprotic organic solvent, is mixed to component (A), and then, component (B) is added thereto.

In the sixth aspect, the present invention provides the process for producing an isocyanurate derivative according to any one of the first to fifth aspects, wherein in the first step, a polyol is added.

DETAILED DESCRIPTION OF THE PREFERRED EMBODIMENTS

Component (A) to be used in the present invention is ris-(2,3-epoxypropyl) isocyanurate containing from 10 to 3,000 ppm of hydrolyzable chlorine. The content of hydrolyzable chlorine contained in tris-(2,3-epoxypropyl) isocyanurate should better be small. However, when tris-(2,3-epoxypropyl) isocyanurate is produced, a compound will usually be formed wherein some of three epoxy groups in the molecule will remain in the form of an ethylene chlorohydrin moiety [—$CH_2CH(OH)CH_2Cl$] as a precursor for an epoxy group, and such a compound will be contained as an impurity in the tris-(2,3-epoxypropyl) isocyanurate product. In the present invention, the tris-(2,3-epoxypropyl) isocyanurate product containing hydrolyzable chlorine derived from such an ethylene chlorohydrin moiety in the above-mentioned proportion, is used as component (A). As such tris-(2,3-epoxypropyl) isocyanurate, a commercial product available under a tradename TEPIC-S (manufactured by Nissan Chemical Industries, Ltd., hydrolyzable chlorine: from 700 to 900 ppm on average) may, for example, be used. The hydrolyzable chlorine can be reduced by repeating recrystallization for a few times, but it is necessary to select the desired starting material taking the labor and costs for recrystallization into consideration.

If the hydrolyzable chlorine in the starting material exceeds 3,000 ppm, ionic chlorine in the isocyanurate derivative is likely to increase substantially due to a slight change in the thermal history, such being undesirable.

The carboxyl group-containing compound to be used for component (B) in the present invention may be at least one member selected from the group consisting of a $C_{2-4}$ monocarboxylic acid, a $C_{2-8}$ polycarboxylic acid and a $C_{2-8}$ hydroxycarboxylic acid. The $C_{2-4}$ monocarboxylic acid may, for example, be formic acid, acetic acid, propionic acid, butyric acid or isobutyric acid. Preferred is acetic acid from the viewpoint of little influence to human bodies, the operation efficiency in view of the boiling point and the low cost. The $C_{2-8}$ polycarboxylic acid may, for example, be oxalic acid, malonic acid, succinic acid or glutaric acid. Preferred is oxalic acid. When such a polycarboxylic acid is used, the viscosity tends to increase substantially, and it is necessary to adjust the amount depending upon the particular purpose. The $C_{2-8}$ hydroxycarboxylic acid may, for example, be hydroxyacetic acid, lactic acid or hydroxybutyric acid. Preferred is lactic acid from the viewpoint of the balance between the water solubility and the oil solubility.

Lactic acid having a purity of 100% can be used. However, lactic acid containing a small amount of water, such as lactic acid having a purity of 90%, may also be useful, since a small amount of water does not substantially react with tris-(2,3-epoxypropyl) isocyanurate and can be removed in a subsequent step of distillation under reduced pressure.

Particularly preferably, the carboxyl group-containing compound of component (B) to be used for the present invention is acetic acid, hydroxyacetic acid, lactic acid or a mixture thereof.

Component (C) to be used in the present invention is an arylphosphine and/or a phosphonium salt comprising a non-halogen anion.

The arylphosphine may, for example, be a triarylphosphine, and triphenylphosphine is, for example, preferably employed.

At the time of producing tris-(2,3-epoxypropyl) isocyanurate, some of three epoxy groups in the molecule will remain in a form of an ethylene chlorohydrin moiety as a precursor for an epoxy group, which will remain as an ethylene chlorohydrin moiety even in an isocyanurate derivative formed by the reaction with a carboxyl group-containing compound. Usually, when reacted with a phosphine in a heated state, the ethylene chlorohydrin moiety forms phosphonium chloride and thus forms ionic chlorine. However, it has been found that with the isocyanurate derivative of the formula (1) containing an ethylene chlorohydrin moiety, produced by the process of the present invention, formation of ionic chlorine is not higher than 1 ppm even when a phosphine is present.

The phosphonium salt comprising a non-halogen anion, comprises a cation such as a tetraarylphosphonium or a triarylalkylphosphonium, and a non-halogen anion. For example, tetraphenylphosphonium borate, triphenylbenzylphosphonium p-toluene sulfonate or triphenylethylphosphonium acetate may be mentioned.

The first step of the present invention is a step of forming a reaction solution containing components (A) and (B) in the presence of component (C) in such a ratio that the carboxyl group in component (B) is from 1.02 to 1.50 mols per mol of the epoxy group in component (A), and then carrying out a reaction until the concentration of the epoxy group in the reaction solution reaches a level of from 0.3 to 0.6 eq/kg (equivalent/kg). In the first step, the temperature control and the time control are not so strict as in the second step, and the reaction is usually carried out at a temperature of from 110 to 130° C. for from 3 to 10 hours.

The above reaction solution comprises components (A), (B) and (C) and may further contain a solvent. The concentration of the epoxy group in the reaction solution is represented by the equivalent amount of the epoxy group based on the total weight of the reaction solution comprising components (A), (B) and (C), or such components plus the solvent.

In the first step, the reaction can be carried out by a first method wherein component (B) having component (C) dissolved therein, is added to component (A), or by a second method wherein component (C) dissolved in an aprotic organic solvent is mixed to component (A) and then component (B) is added thereto.

The first method wherein component (B) having component (C) dissolved therein, is added to component (A), is preferred, since towards the end of the reaction, component (B) will be consumed so that the catalyst concentration will increase.

If component (C) is mixed, without being preliminarily dissolved, to molten tris-(2,3-epoxypropyl) isocyanurate, polymerization of tris-(2,3-epoxypropyl) isocyanurate is likely to take place at the interface of the catalyst particles of component (C) which is not partially dissolved, to form insoluble polymer particles, such being undesirable.

In the first step, a polyol may be added. As such a polyol, ethylene glycol, propylene glycol or butane diol is, for example, preferred. The amount is preferably from 3 to 20 wt% in the reaction solution. Such a polyol has a merit such that the initial reaction rate of tris-(2,3-epoxypropyl) isocyanurate with the carboxyl group-containing compound, can be moderated without affecting the overall reaction time required. This mechanism is not clearly understood, but it may be such that the active sites for chemical reaction at the initial stage are moderated by a chelating action of the polyol.

The amount of the total carboxyl group-containing compounds may be classified into the following two cases depending upon the particular application. Namely, in an application wherein the epoxy concentration in the final product is required to be less than 0.1 eq/kg, like the isocyanurate derivative of the formula (1) obtainable by the present invention, it is preferred to add at least one carboxyl group-containing compound in a ratio corresponding to from 1.02 to 1.50 mols, particularly preferably from 1.05 to 1.30 mols, of the carboxyl group per mol of the epoxy group.

On the other hand, in an application where the obtainable isocyanurate derivative can be used without any problem even if the epoxy concentration in the final product is from 0.3 to 1.8 eq/kg, it is preferred to add at least one carboxyl group-containing compound corresponding to from 0.70 to 0.95 mol of the carboxyl group per mol of the epoxy group.

The second step of the present invention is a step of maintaining the reaction solution at a temperature within a range of from 80 to 130° C. for H hours, provided $0.2 \times 2.5^n \leq H \leq 2 \times 2.5^n$, where $n=0.1(110-T)$ where T is the temperature (° C.), to bring the concentration of the epoxy group in the reaction solution to a level of less than 0.1 eq/kg.

It is advisable to reduce the thermal history as far as possible once the concentration of the epoxy group has decreased to a certain level. When the concentration of the epoxy group is high, ionic chlorine scarcely forms, but when the concentration of the epoxy group lowers, the hydrolyzable chlorine gradually undergoes a dehydrochlorination reaction and changes to ionic chlorine. This phenomenon may be such that ionic chlorine formed by thermal decomposition of the hydrolyzable chlorine, will react with the epoxy group present in a large amount and will return to hydrolyzable chlorine of an ethylene chlorohydrin type.

The concentration of the epoxy group required for the ionic chlorine to return to hydrolyzable chlorine substantially, was determined by various studies, and as a result, it has been found that when the concentration of the epoxy group in the reaction solution is higher than 0.3 eq/kg, there will be no substantial formation of ionic chlorine. Namely, it has been found that if the concentration of the epoxy group in the reaction solution has decreased to a level of less than 0.3 eq/kg, particularly less than 0.1 eq/kg, the hydrolyzable chlorine will gradually be decomposed to ionic chlorine. Further, as a result of a comparison between the temperature dependency of the formation of ionic chlorine and the temperature dependency of the intended addition reaction of the epoxy group with the carboxyl group-containing compound, it has been found that the former is higher by about 1.2 times, and accordingly, as the temperature increases, the proportion for the formation of ionic chlorine tends to be higher than the desired addition reaction rate, such being disadvantageous.

The maintenance in the second step applies to the entire post treatment step including a step of reducing the concentration of the epoxy group in the reaction solution to a level of less than 0.1 eq/kg, which corresponds to a substantial completion of the reaction and a step for distillation under reduced pressure of the carboxyl group-containing compound and is required to be carried out at a treating temperature of from 80 to 130° C. for an allowable time H (hr) within a range represented by the following formula: $0.2 \times 2.5^n \leq H \leq 2 \times 2.5^n$ where $n=0.1(110-T)$, where T is the temperature (° C.).

In the following Table, specific examples for the treating temperature and the allowable time in the second step, will be given.

TABLE 1

| Treating temperature (° C.) | Allowable time (hr) |
|---|---|
| 130 | 0.03 to 0.32 |
| 120 | 0.08 to 0.80 |
| 115 | 0.13 to 1.26 |
| 110 | 0.20 to 2.00 |
| 105 | 0.32 to 3.16 |
| 100 | 0.50 to 5.00 |
| 95 | 0.79 to 7.91 |
| 90 | 1.25 to 12.5 |
| 80 | 3.13 to 31.3 |

As is evident from the above Table, at a temperature of 80° C. or lower, the allowable time increases to a large extent. Accordingly, at a stage where the concentration of the epoxy group is low, it is important to reduce a process wherein the compound is exposed at a high temperature, as far as possible, to prevent formation of ionic chlorine.

Firstly, with respect to lowering of the temperature or shortening of the time at the final stage of the reaction, for example, around the terminal point of the reaction, both the epoxy group concentration and the acid concentration will decrease, whereby the reaction rate will decrease substantially. If it is attempted to carry out the reaction completely, it takes time, and ionic chlorine will increase during the reaction time. If either one is set to be slightly excessive, the reaction rate will increase. If tris-(2,3-epoxypropyl) isocyanurate is set to be excessive, it is likely to remain as an unreacted substance in the product and thus is likely to impair the desired properties. On the other hand, if the carboxyl group-containing compound is used excessively, it can be distilled off under high vacuum after the reaction, such being preferred. In such a case, it is necessary to pay attention to the fact that if the excessive degree of the carboxyl group-containing compound is too much, a secondary alcohol formed by the reaction of the epoxy group and the carboxyl group, is likely to further bring about an esterification reaction with a carboxyl group.

The amount of the catalyst of component (C) is preferably from 0.05 to 2 wt % based on the entire reaction solution. If the amount is less than this range, the reaction rate at the final stage of the reaction tends to be low, and the reaction time has to be prolonged substantially, whereby ionic chlorine is likely to increase. If the amount exceeds the above range, the initial reaction rate tends to be so high that the temperature control tends to be difficult. Accordingly, the amount may be large if a system of gradually adding a necessary amount is adopted. If the amount is too much, depending upon the particular application, an adverse effect of the residual catalyst may appear to impair the desired properties.

It is also important to carry out the reaction in the absence of a solvent, or to reduce the thermal history in the step of distilling off the solvent for the reaction by employing a solvent for the reaction which can be distilled off at a low temperature.

If the reaction is carried out in the absence of a solvent from the initial stage, dissolution of tris-(2,3-epoxypropyl) isocyanurate will be slow, and the temperature control tends to be difficult on an industrial scale. Accordingly, it is conceivable to adopt a method wherein a solvent is initially added, and the solvent is gradually distilled off. However, the carboxyl group-containing compound will also be distilled off together with the solvent, and supplemental addition of the compound will be required.

The most preferred method is a method of using a solvent which has a boiling point in the vicinity of from 80 to 130° C. and which does not react with tris-(2,3-epoxypropyl) isocyanurate.

By the use of a solvent for the reaction, the temperature control will be facilitated, since the substrate concentration is thereby lowered to smooth the reaction, and since a large amount of the reaction heat will be thereby dissipated. Further, if a solvent having a boiling point for refluxing in the vicinity of the reaction temperature, is employed, even if an abrupt heat generation occurs, the temperature may not increase beyond the boiling point, whereby the temperature control will be very easy.

The amount of the solvent for the reaction is preferably from 2 to 50 wt %, based on the entire reaction solution. If it is less than this range, the effects tend to be weak, and if it exceeds this range, the overall reaction time tends to be prolonged, and an excess time will be required for distillation of the solvent, such being undesirable.

In the first and second methods in the first step, a solvent for the reaction can be used. The solvent for the reaction is not particularly limited so long as it does not substantially react with tris-(2,3-epoxypropyl) isocyanurate. However, an aprotic organic solvent is preferred. For example, as an aromatic solvent, toluene, benzene or xylene is preferred. As a ketone solvent, methyl ethyl ketone or isobutyl ketone is preferred. As an ester solvent, ethyl acetate, propyl acetate or butyl acetate is, for example, preferred. As a cellosolve solvent, methyl cellosolve is preferred, and as a polyol solvent, ethylene glycol or propylene glycol will not substantially react and may accordingly be used.

It is also important to suppress polymerization of tris-(2, 3-epoxypropyl) isocyanurate which causes an insoluble substance and thereby to omit hot filtration. When a tertiary amine or a quaternary ammonium salt is used as a catalyst, or the reaction is carried out at a high temperature in the absence of a catalyst, an insoluble polymer of tris-(2,3-epoxypropyl) isocyanurate is likely to form as a by-product, whereby hot filtration at a relatively high temperature will be required, such being undesirable.

If the phosphine or the phosphonium salt is used in a dissolved state, the desired addition reaction can be selectively promoted without bringing about polymerization of tris-(2,3-epoxypropyl) isocyanurate, whereby hot filtration will be unnecessary. If it is directly added to molten triglycidyl isocyanurate, it will not completely be dissolved and is likely to cause a decrease in the catalytic activities or formation of an insoluble substance as a by-product.

Treatment at a high temperature for a long time in the second step of the present invention brings about a problem that a part of hydrolyzable chlorine undergoes decomposition to form ionic chlorine as a by-product. Further, if a halide is used as a quaternary onium salt, and if it remains in the product, it will adversely affect the electrical properties, as it is ionic chlorine. Further, in a case where no catalyst is employed, a reaction at a relatively high temperature will be necessary, whereby a part of hydrolyzable chlorine will decompose and form ionic chlorine from the time when the epoxy group concentration has decreased, and such ionic chlorine tends to increase in the isocyanurate derivative as the product.

The product of the formula (1) obtainable from the second step is a transparent highly viscous liquid having ionic chlorine content of from 0.1 to 5 ppm and being free from an insoluble substance.

In the isocyanurate derivative of the formula (1) obtainable by the present invention, if, for example, acetic acid is used as component (B), either one of $X^1$ and $X^2$ is a $CH_3COO$ group and the other is a OH group, either one of $Y^1$ and $Y^2$ is a $CH_3COO$ group and the other is a OH group, and further, either one of $Z^1$ and $Z^2$ is a $CH_3COO$ group and the other is a OH group. Further, if, for example, a hydroxyacetic acid is used as component (B), either one of $X^1$ and $X^2$ is a $CH_2(OH)COO$ group and the other is a OH group, either one of $Y^1$ and $Y^2$ is a $CH_2(OH)COO$ group and the other is a OH group, and further, either one of $Z^1$ and $Z^2$ is a $CH_2(OH)COO$ group and the other is a OH group. Further, if, for example, lactic acid is used as component (B), either one of $X^1$ and $X^2$ is a $CH_3CH(OH)COO$ group and the other is a OH group, either one of $Y^1$ and $Y^2$ is a $CH_3CH(OH)COO$ group and the other is a OH group, and further, either one of $Z^1$ and $Z^2$ is a $CH_3CH(OH)COO$ group and the other is a OH group.

In the present invention, the hydrolyzable chlorine content is measured by a method wherein 1 g of a sample is accurately weighed and dissolved in 60 g of dioxane, and 10 ml of a 1N potassium hydroxide ethanol solution is added thereto, followed by heating for 30 minutes under reflux. After diluting it with 100 mi of a water +acetone (1:1) solution, it is acidified with 2 ml of concentrated nitric acid and then subjected to potentiometric titration with a 0.002N silver nitrate aqueous solution.

The ionic chlorine content is measured by a method wherein 10 g of a sample is accurately weighed and dissolved in 60 g of acetone, 10 g of methanol and 5 g of pure water, and after acidifying it with 2 ml of concentrated nitric acid, it is subjected to potentiometric titration with a 0.002N silver nitrate aqueous solution.

The epoxy group concentration (eq/kg) is measured by a method wherein 1 g of a sample is accurately weighed and dissolved in 60 g of a titration solution and subjected to potentiometric titration with a 0.1N perchloric acid-acetic acid standard solution. Here, the titration solution is a dissolved solution of 60 g of tetraethylammonium bromide +500 g of acetic acid +500 g of acetone.

The acid content (eq/kg) is measured by a method wherein 1 g of a sample is accurately weighed and dissolved in 30 g of acetone and 30 g of water, and the solution is subjected to potentiometric titration with a 0.1N potassium hydroxide standard solution.

Now, the present invention will be described in further detail with reference to Examples. However, it should be understood that the present invention is by no means restricted to such specific Examples.

EXAMPLE 1

First step: In a nitrogen atmosphere, 3,000 g (30 equivalents as the epoxy group) of tris-(2,3-epoxypropyl) isocyanurate (TEPIC-S, tradename, manufactured by Nissan Chemical Industries, Ltd., containing 700 ppm of hydrolyzable chlorine) was melted at 130° C., and then cooled once to a level of from 115 to 120° C. While maintaining it at that temperature, a solution prepared by dissolving 5 g of triphenylphosphine in 120 g of toluene in a separate container and further dissolving 1,720 g of acetic acid (28.7 equivalents as the carboxyl group) therein, was dropwise added over a period of 4 hours. Further, 300 g of lactic acid having a purity of 90% (3 equivalents as the carboxyl group) was dropwise added thereto over a period of one hour. Then, the mixture was heated at a temperature of from 115 to 120° C. for two hours. At this stage, sampling was carried out, whereby the epoxy group concentration was 0.36 (eq/kg).

Second step: The reaction solution was maintained at a temperature of 100° C. under reduced pressure for 3.5 hours including distillation of toluene and unreacted acetic acid. The obtained product was a slightly yellow transparent highly viscous liquid free from an insoluble substance, wherein the ionic chlorine was 1 ppm, the acid content (the carboxyl group content) was 0.4 (eq/kg), and the epoxy group concentration was 0.02 (eq/kg).

EXAMPLE 2

First step: In a nitrogen atmosphere, 3,000 g (30 equivalents as the epoxy group) of tris-(2,3-epoxypropyl) isocyanurate (TEPIC-S, tradename, manufactured by Nissan Chemical Industries, Ltd., containing 700 ppm of hydrolyzable chlorine) was dissolved in 480 g of toluene at 110 to 120° C. Then, a solution separately prepared by dissolving 5 g of triphenylphosphine in 120 g of toluene and further dissolving 1,720 g of acetic acid (28.7 equivalents as the carboxyl group) therein, was dropwise added thereto over a period of 4 hours. Further, 300 g of lactic acid having a purity of 90% (3 equivalents as the carboxyl group) was dropwise added thereto over a period of one hour. Then, the mixture was heated at a temperature of from 115 to 120° C. for 3 hours. At this stage, sampling was carried out, whereby the epoxy group concentration was 0.33 (eq/kg).

Second step: The reaction solution was maintained at a temperature of 100° C. under reduced pressure for 4.5 hours including distillation of toluene and unreacted acetic acid. The obtained product was a slightly yellow transparent highly viscous liquid free from an insoluble substance, wherein the ionic chlorine was 2 ppm, the acid content (the carboxyl group content) was 0.4 (eq/kg), and the epoxy group concentration was 0.02 (eq/kg).

EXAMPLE 3

First step: In a nitrogen atmosphere, 3,000 g (30 equivalents as the epoxy group) of tris-(2,3-epoxypropyl) isocyanurate (TEPIC-S, tradename, manufactured by Nissan Chemical Industries, Ltd., containing 700 ppm of hydrolyzable chlorine) was melted at 130° C., and then cooled once to a level of from 115 to 120° C. While maintaining it at that temperature, a solution prepared by dissolving 5 g of triphenylphosphine in 120 g of toluene in a separate container and further dissolving 2,340 g of acetic acid (39 equivalents as the carboxyl group) therein, was dropwise added over a period of 6 hours. Further, 300 g of lactic acid having a purity of 90% (3 equivalents as the carboxyl group) was dropwise added thereto over a period of 30 minutes. Then, the mixture was heated at 115° C. for two hours. At this stage, sampling was carried out, whereby the epoxy group concentration was 0.32 (eq/kg).

Second step: The reaction solution was maintained at a temperature of 100° C. under reduced pressure for 3.5 hours including distillation of toluene and unreacted acetic acid. The obtained product was a slightly yellow transparent highly viscous liquid free from an insoluble substance, wherein the ionic chlorine was 1 ppm, the acid content (the carboxyl group content) was 0.6 (eq/kg), and the epoxy group concentration was 0.01 (eq/kg).

EXAMPLE 4

First step: In a nitrogen atmosphere, 3,000 g (30 equivalents as the epoxy group) of tris-(2,3-epoxypropyl) isocyanurate (TEPIC-S, tradename, manufactured by Nissan Chemical Industries, Ltd., containing 700 ppm of hydrolyzable chlorine) was melted at 130° C., and then cooled once to a level of from 115 to 120° C. While maintaining it at that temperature, a solution prepared by dissolving 5 g of triphenylphosphine in 120 g of toluene in a separate container and further dissolving 1,476 g of acetic acid (24.6 equivalents as the carboxyl group) therein, was dropwise added over a period of 4 hours. Further, 300 g of lactic acid having a purity of 90% (3 equivalents as the carboxyl group) was dropwise added thereto over a period of 30 minutes. Then, the mixture was heated at a temperature of from 115 to 120° C. for 4 hours, whereupon an insoluble substance was slightly observed. At this stage, sampling was carried out, whereby the epoxy group concentration was 0.46 (eq/kg).

Second step: The reaction solution was maintained at a temperature of 110° C., and in that state, the solution was passed through a filtration machine of 500 mesh to remove the insoluble substance over a period of one hour. The obtained product was a slightly yellow transparent highly viscous liquid free from an insoluble substance, wherein the ionic chlorine was 5 ppm, the acid content (the carboxyl group content) was 0.02 (eq/kg), and the epoxy group concentration was 0.44 (eq/kg).

EXAMPLE 5

First step: In a nitrogen atmosphere, 3,000 g (30 equivalents as the epoxy group) of tris-(2,3-epoxypropyl) isocyanurate (TEPIC-S, tradename, manufactured by Nissan Chemical Industries, Ltd., containing 700 ppm of hydrolyzable chlorine) was melted at 130° C., and then once cooled to a level of from 115 to 120° C. While maintaining it at that temperature, a solution prepared by dissolving 5 g of triphenylphosphine in 120 g of toluene in a separate container and further dissolving 1,720 g of acetic acid (28.7 equivalents as the carboxyl group), was dropwise added over a period of 4 hours. Further, 228 g of hydroxyacetic acid having a purity of 100% (3 equivalents as the carboxyl group) was dropwise added thereto over a period of one hour. Then, the mixture was heated at a temperature of from 115 to 120° C. for two hours. At this stage, sampling was carried out, whereby the epoxy group concentration was 0.36 (eq/kg).

Second step: The reaction solution was reacted at a temperature of 100° C. under reduced pressure for 3 hours including distillation of toluene and unreacted acetic acid. The obtained product was a slightly yellow transparent highly viscous liquid free from an insoluble substance, wherein the ionic chlorine was 1 ppm, the acid content (the carboxyl group content) was 0.5 (eq/kg), and the epoxy group concentration was 0.03 (eq/kg).

COMPARATIVE EXAMPLE 1

First step: In a nitrogen atmosphere, 3,000 g (30 equivalents as the epoxy group) of tris-(2,3-epoxypropyl) isocyanurate (TEPIC-S, tradename, manufactured by Nissan Chemical Industries, Ltd., containing 700 ppm of hydrolyzable chlorine) was melted at 130° C., and then once cooled to a temperature of from 115 to 120° C. While maintaining it at that temperature, a solution prepared by dissolving 5 g of triphenylphosphine in 120 g of toluene and further mixing and dissolving 1,720 g of acetic acid (28.7 equivalents as the carboxyl group) therein, was dropwise added over a period of 4 hours. Further, 300 g of lactic acid having a purity of 90% (3 equivalents as the carboxyl group) was dropwise added thereto over a period of one hour. Then, the mixture was heated at a temperature of from 115 to 120° C. for 3 hours. At this stage, sampling was carried out, whereby the epoxy group concentration was 0.31 (eq/kg).

Second step: The reaction solution was reacted at a temperature of 115° C. under reduced pressure for 3.5 hours, including distillation of toluene and unreacted acetic acid. The obtained product was a slightly yellow transparent highly viscous liquid free from an insoluble substance, wherein the ionic chlorine was 7 ppm, the acid content (the carboxyl group content) was 0.4 (eq/kg), and the epoxy group concentration was 0.02 (eq/kg).

COMPARATIVE EXAMPLE 2

First step: In a nitrogen atmosphere, 3,000 g (30 equivalents as the epoxy group) of tris-(2,3-epoxypropyl) isocyanurate (TEPIC-S, tradename, manufactured by Nissan Chemical Industries, Ltd., containing 700 ppm of hydrolyzable chlorine) and 5 g of tetramethylammonium chloride, were melted and mixed at 130° C., and then once cooled to a level of from 115 to 120° C. While maintaining the mixture at that temperature, 1,720 g of acetic acid (28.7 equivalents as the carboxyl group) was dropwise added over a period of 4 hours. Further, 300 g of lactic acid having a purity of 90% (3 equivalents as the carboxyl group) was dropwise added thereto over a period of one hour. Then, the mixture was heated at a temperature of from 115 to 120° C. for two hours. At this stage, sampling was carried out, whereby the epoxy group concentration was 0.42 (eq/kg).

Second step: The solution was maintained at a temperature of 100° C. for further 3.5 hours. The obtained product was a slightly yellow opaque highly viscous liquid containing a large amount of an insoluble substance. Therefore, the product was maintained at a temperature of 110° C. to lower the viscosity, and in that state, it was passed through a filtration machine of 400 mesh to remove the majority of the insoluble substance over a period of 4 hours. The product was a slightly turbid highly viscous liquid, wherein the ionic chlorine was 300 ppm, the acid content (the carboxyl group content) was 0.3 (eq/kg), and the epoxy group concentration was 0.02 (eq/kg).

COMPARATIVE EXAMPLE 3

First step: 3,160 g (30 equivalents as the epoxy group) of tris-(2,3-epoxypropyl) isocyanurate (TEPIC-G, tradename, manufactured by Nissan Chemical Industries, Ltd., containing 7,000 ppm of hydrolyzable chlorine) was melted in a nitrogen atmosphere at 130° C., and then once cooled to a level of from 115 to 120° C. While maintaining it at that temperature, a solution prepared by dissolving 5 g of triphenylphosphine in 120 g of toluene in a separate container and further mixing and dissolving 1,720 g of acetic acid (28.7 equivalents as the carboxyl group), was dropwise added over a period of 4 hours. Further, 300 g of lactic acid having a purity of 90% (3 equivalents as the carboxyl group) was dropwise added thereto over a period of one hour. Then, the mixture was heated at a temperature of from 115 to 120° C. for two hours. At this stage, sampling was carried out, whereby the epoxy group concentration was 0.33 (eq/kg).

Second step: The solution was maintained at a temperature of 100° C. under reduced pressure for 3.5 hours, including distillation of toluene or unreacted acetic acid. The obtained product was a slightly yellow transparent highly viscous liquid free from an insoluble substance, wherein the ionic chlorine was 17 ppm, the acid content (the carboxyl group content) was 0.4 (eq/kg), and the epoxy group concentration was 0.02 (eq/kg).

COMPARATIVE EXAMPLE 4

First step: In a nitrogen atmosphere, 3,000 g (30 equivalents as the epoxy group) of tris-(2,3-epoxypropyl) isocyanurate (TEPIC-S, tradename, manufactured by Nissan Chemical Industries, Ltd., containing 700 ppm of hydrolyzable chlorine) was melted at 130° C., and then once cooled to a level of from 115 to 120° C. While maintaining it at that temperature, a solution prepared by dissolving 5 g of triphenylphosphine in 120 g of toluene and then further mixing and dissolving 1,720 g of acetic acid (28.7 equivalents as the carboxyl group) therein, was dropwise added over a period of 4 hours. Further, 300 g of lactic acid having a purity of 90% (3 equivalents as the carboxyl group) was dropwise added thereto over a period of one hour. Then, the mixture was heated at a temperature of from 115 to 120° C. for 3 hours. At this stage, sampling was carried out, whereby the epoxy value was 0.31 (eq/kg).

Second step: The temperature was lowered to 105° C., and the solution was maintained under reduced pressure for 10 hours, including distillation of toluene and unreacted acetic acid. The obtained product was a slightly yellow transparent highly viscous liquid free from an insoluble substance, wherein the ionic chlorine as 12 ppm, the acid content (the carboxyl group content) as 0.4 (eq/jkg), and the epoxy group concentration was 0.02 (eq/kg).

COMPARATIVE EXAMPLE 5

First step: In a nitrogen atmosphere, 3,000 g (30 equivalents as the epoxy group) of tris-(2,3-epoxypropyl) isocyanurate (TEPIC-S, tradename, manufactured by Nissan Chemical Industries, Ltd., containing 700 ppm of hydrolyzable chlorine) was melted at 130° C., and then while maintaining it at that temperature, 1,720 g of acetic acid (28.7 equivalents as the carboxyl group) was dropwise added over a period of 4 hours. Further, 300 g of lactic acid having a purity of 90% (3 equivalents as the carboxyl group) was dropwise added thereto over a period of one hour. Then, the mixture was heated at 130° C. for 4 hours. At this stage, sampling was carried out, whereby the epoxy group concentration was 0.38 (eq/kg).

Second step: The solution was reacted at a temperature of 120° C. under reduced pressure for 3 hours, including distillation of unreacted acetic acid. The obtained product was a slightly yellow opaque highly viscous liquid containing an insoluble substance. Therefore, it was maintained at a temperature of 110° C., and in that state, it was passed through a filtration machine of 500 mesh to remove the majority of the insoluble substance over a period of two hours. The product was a slightly turbid highly viscous liquid, wherein the ionic chlorine was 25 ppm, the acid content (the carboxyl group content) was 0.5 (eq/kg), and the epoxy group concentration was 0.03 (eq/kg).

COMPARATIVE EXAMPLE 6

First step: In a nitrogen atmosphere, 3,000 g (30 equivalents as the epoxy group) of tris-(2,3-epoxypropyl) isocyanurate (TEPIC-S, tradename, manufactured by Nissan Chemical Industries, Ltd., containing 700 ppm of hydrolyzable chlorine) and 5 g of triphenylphosphine were melt-mixed at 130° C., but were not completely dissolved. The mixture was cooled once to a level of from 115 to 120° C., and while maintaining it at that temperature, 1,720 g of acetic acid (28.7 equivalents as the carboxyl group) was dropwise added over a period of 4 hours. Further, 300 g of lactic acid having a purity of 90% (3 equivalents as the carboxyl group) was dropwise added thereto over a period of one hour. Then, the mixture was heated at a temperature of from 115 to 120° C. for 4 hours. At this stage, sampling was carried out, whereby the epoxy group concentration was 0.42 (eq/kg).

Second step: The solution was further reacted at a temperature of 100° C. for 7 hours. The obtained product was a slightly yellow transparent highly viscous liquid containing a small amount of an insoluble substance. Therefore, it was heated to 110° C. to lower the viscosity, and in that state, it was passed through a filtration machine of 400 mesh to remove the majority of the impurity over a period of two hours. The product was a slightly turbid highly viscous liquid, wherein the ionic chlorine was 7 ppm, the acid content (the carboxyl group content) was 0.5 (eq/kg), and the epoxy group concentration was 0.03 (eq/kg).

When tris-(2,3-epoxypropyl) isocyanurate is produced, a compound wherein some of three epoxy groups in the molecule will remain in the form of an ethylene chlorohydrin moiety [—$CH_2CH(OH)CH_2Cl$] as a precursor for an epoxy group, is present as an impurity. The epoxy compound having such an ethylene chlorohydrin moiety will still remain as ethylene chlorohydrin as it is, even in an isocyanurate derivative formed by its reaction with a carboxyl group-containing compound. In the process for producing the isocyanurate derivative, the ethylene chlorohydrin moiety will undergo dehydrochlorination depending upon the condition if the epoxy group concentration decreases, and will remain as an ionic chlorine atom in the isocyanurate derivative as the product. When such an isocyanurate derivative is used in the electrical field, the ionic chlorine atom will bring about an adverse effect.

According to the present invention, in the process for producing an isocyanurate derivative of the formula (1), the reaction is carried out under a condition to satisfy a specific thermal history (relation between the temperature and the time) when the epoxy group concentration in the reaction solution becomes to be less than 0.1 eq/kg, whereby the ionic chlorine atom in the isocyanurate derivative of the formula (1) obtainable as the product, can be brought to an extremely low level of from 0.1 to 5 ppm.

What is claimed is:

1. A process for producing an isocyanurate derivative of the formula (1):

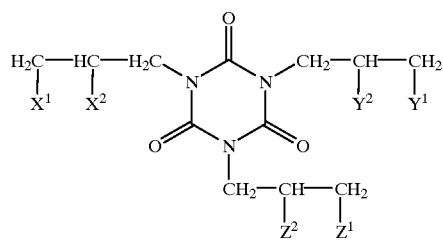

(1)

wherein either one of $X^1$ and $X^2$ is a $R^1COO$ group and the other is a OH group, either one of $Y^1$ and $Y^2$ is a $R^2COO$ group and the other is a OH group, either one of $Z^1$ and $Z^2$ is a $R^3COO$ group and the other is a OH group, and each of $R^1$, $R^2$ and $R^3$ is a $C_{1-7}$ organic group, having an ionic chlorine atom content of from 0.1 to 5 ppm, which comprises a first step of forming a reaction solution containing (A) tris-(2,3-epoxypropyl) isocyanurate containing from 10 to 3,000 ppm of hydrolyzable chlorine and (B) a $C_{2-8}$ carboxyl group-containing compound in the presence of (C) an arylphosphine and/or a phosphonium salt comprising a non-halogen anion, in such a ratio that the carboxyl group in component (B) is from 1.02 to 1.50 mols per mol of the epoxy group in component (A), and then carrying out a reaction until the concentration of the epoxy group in the reaction solution decreases to a level of from 0.3 to 0.6 eq/kg, and a second step of maintaining the reaction solution at a temperature within a range of from 80 to 130° C. for H hours, wherein $0.2 \times 2.5^n \leq H \leq 2 \times 2.5^n$, where n=0.1(110−T) where T is the temperature (° C.), to bring the concentration of the epoxy group in the reaction solution to a level of less than 0.1 eq/kg.

2. The process for producing an isocyanurate derivative according to claim 1, wherein the carboxyl group-containing compound of component (B) is at least one member selected from the group consisting of a $C_{2-4}$ monocarboxylic acid, a $C_{2-8}$ polycarboxylic acid and a $C_{2-8}$ hydroxycarboxylic acid.

3. The process for producing an isocyanurate derivative according to claim 1, wherein the carboxyl group-containing compound of component (B) is acetic acid, hydroxyacetic acid, lactic acid, or a mixture thereof.

4. The process for producing an isocyanurate derivative according to claim 1, wherein in the first step, the reaction is carried out in such a manner that component (B) having component (C) dissolved therein, is added to component (A).

5. The process for producing an isocyanurate derivative according to claim 1, wherein in the first step, the reaction is carried out in such a manner that component (C) dissolved in an aprotic organic solvent, is mixed to component (A), and then, component (B) is added thereto.

6. The process for producing an isocyanurate derivative according to claim 1, wherein in the first step, a polyol is added.

7. The process according to claim 3, wherein a solution containing triphenylphosphine as component (C) and acetic acid is added to component (A) to react therewith and thereafter lactic acid or hydroxyacetic acid is added to react therewith to continue the reaction.

* * * * *